(12) United States Patent
Spro et al.

(10) Patent No.: US 10,709,637 B2
(45) Date of Patent: Jul. 14, 2020

(54) VENOUS BAG CLAMPING MECHANISM

(71) Applicant: Sorin Group Italia S.r.l., Milan (IT)

(72) Inventors: Stefano Spro, Calimera (IT); Stefano Reggiani, Medolla (IT); Claudio Silvestri, Quarantoli Mirandola (IT); Francesco Benatti, Concordia S.S. (IT); Adriano Mazzoli, San Felice S.P. (IT)

(73) Assignee: Sorin Group Italia S.r.l., Milan (IT)

( * ) Notice: Subject to any disclaimer, the term of this patent is extended or adjusted under 35 U.S.C. 154(b) by 387 days.

(21) Appl. No.: 15/529,933

(22) PCT Filed: Nov. 26, 2014

(86) PCT No.: PCT/IB2014/066355
§ 371 (c)(1),
(2) Date: May 25, 2017

(87) PCT Pub. No.: WO2016/083867
PCT Pub. Date: Jun. 2, 2016

(65) Prior Publication Data
US 2017/0326030 A1    Nov. 16, 2017

(51) Int. Cl.
*A61J 1/10*        (2006.01)
*A61J 1/14*        (2006.01)
(Continued)

(52) U.S. Cl.
CPC ............... *A61J 1/10* (2013.01); *A61J 1/1481* (2015.05); *A61J 1/1487* (2015.05);
(Continued)

(58) Field of Classification Search
CPC ...... A61J 1/10; A61J 1/1481; A61M 2209/08; A61M 39/105; A61M 39/28; A61M 5/14
See application file for complete search history.

(56) References Cited

U.S. PATENT DOCUMENTS 5,061,236 A * 10/1991 Sutherland .......... A61M 1/3627
                                                    210/436
5,328,461 A    7/1994 Utterberg
(Continued)

FOREIGN PATENT DOCUMENTS

| JP | H06502777 A | 3/1994 |
| JP | 2003530160 A | 10/2003 |
| WO | WO2001076656 A2 | 10/2001 |

OTHER PUBLICATIONS

International Preliminary Report on Patentability issued in PCT/IB2014/066355, dated Jun. 8, 2017, 15 pages.
(Continued)

*Primary Examiner* — Leslie R Deak
(74) *Attorney, Agent, or Firm* — Faegre Drinker Biddle & Reath LLP (57) ABSTRACT

A venous reservoir including a single inlet line clamp capable of partially or completely restricting blood flow to the venous reservoir. The venous reservoir is provided with a rigid back plate or bracket that can accommodate an inlet line capable of joining to at least one blood inlet port. The rigid back plate or bracket can accommodate a clamp capable of completely or partially closing the inlet line containing both the cardiotomy line and the venous line to manually control the blood flow drained from the patient.

12 Claims, 4 Drawing Sheets

(51) Int. Cl.
    *A61M 1/36*        (2006.01)
    *A61M 39/10*      (2006.01)
    *A61M 39/28*      (2006.01)
    *A61M 5/14*        (2006.01)

(52) U.S. Cl.
    CPC ........ *A61M 1/3627* (2013.01); *A61M 39/105* (2013.01); *A61M 39/28* (2013.01); *A61M 5/14* (2013.01); *A61M 2209/08* (2013.01)

(56) References Cited

U.S. PATENT DOCUMENTS

| | | |
|---|---|---|
| 5,573,526 A | 11/1996 | Hess |
| 5,580,349 A | 12/1996 | Thor et al. |
| 5,693,039 A | 12/1997 | Stewart et al. |
| 5,858,015 A | 1/1999 | Fini |
| 6,105,912 A | 8/2000 | Lindsay et al. |
| 2007/0293804 A1 | 12/2007 | Ghelli et al. |
| 2014/0271358 A1 | 9/2014 | Samolyk |

OTHER PUBLICATIONS

International Search Report arid Written Opinion issued in PCT/IB2014/066355, dated Jul. 15, 2015, 17 pages.

\* cited by examiner

VENOUS BAG CLAMPING MECHANISM

CROSS-REFERENCE TO RELATED APPLICATION

This application is a national stage application of PCT/IB2014/066355, filed Nov. 26, 2014, which is herein incorporated by reference in its entirety.

TECHNICAL FIELD

The present invention relates to medical devices and methods for controlling extracorporeal blood handling. More specifically, the present invention relates to a blood venous collapsible reservoir (said here reservoir bag) that can hold a selectively variable amount of blood and methods for controlling blood flow into the reservoir bag.

BACKGROUND

During many types of surgical procedures, for example, open heart surgery, blood is removed from the patient and passed through an extracorporeal circuit for oxygenation and filtration. As the blood that has been removed from the patient passes through the extracorporeal circuit, it may be temporarily stored in an extracorporeal reservoir. One such reservoir used to temporarily hold blood is a venous reservoir. Venous reservoirs are constructed to allow for easy venting of air from the reservoir and may include a mesh to filter blood as it passes through the reservoir. Venous reservoirs may be rigid (hard shell) or soft shell (bag).

Soft shell venous reservoirs are devices used in extracorporeal circulation during cardiotomy procedures as containers for holding blood coming from the venous cannulation of the patient and from an external cardiotomy reservoir that is dedicated to handle blood from the field suckers. In some instances, during operation, it may be necessary to temporarily divert venous blood into a cardiotomy reservoir for storage, instead of the soft shell reservoir.

Soft shell reservoirs have at least one wall constructed from a soft material, for example a plastic sheet. They are typically comprised from a soft bag constructed as a closed system that can change shape depending on the amount of blood stored in them. One advantage of a soft shell reservoir or "bag" is that it will collapse when emptied, thus preventing accidental delivery of air to the patient. Another advantage is that the contact between air and blood in a soft shell reservoir is very limited, thus reducing blood activation during extracorporeal circulation.

Blood flowing into the bag is carried through an inlet port that is typically located near the bottom of the bag. Blood flowing out of the bag is carried out through an outlet port that may be connected to an outlet tube. The outlet port is typically located near the bottom of the bag.

Between the inlet port and outlet port there may be a filter for filtering the blood and removing any solid and gaseous micro-emboli or air. Air that is removed from the blood can gather at the top of the bag and be vented out. There is typically at least one port near the top of the bag to allow air from the blood to exit the bag.

SUMMARY

It is an object of the current invention to provide an easy way to clamp off the venous reservoir using only one clamp. Using a single clamp allows for employment of an intuitive maneuver thus reducing the problems such as perfusionist mistakes and tube crowding that were previously described.

To meet this objective, a clamp is located at the inlet line for the venous bag to allow a healthcare worker to completely or partially seal the blood flow into the venous reservoir. The clamp is located downstream from a Y connector that the venous line and the cardiotomy line are connected to.

The current invention is a soft shell venous reservoir for use in a cardiotomy system of the type including a blood reservoir comprising at least a first layer of flexible material and a second layer. The first and second layer are sealed together to define a bag compartment capable of receiving fluid. The bag compartment has openings defining a first flow port, a second flow port, and an air vent. A flexible tube is in fluid communication with the first flow port. A rigid back plate contains securements to couple the blood reservoir, the first flow port, and the flexible tube to the rigid back plate. And a manual or automatic clamp can be situated at the flexible tube, such that a healthcare worker can engage the clamp to control the fluid flow rate between the rigid tube connector and the first flow port.

The clampable soft shell venous reservoir comprises a blood reservoir having a first and second layer of flexible material sealed together to define a bag compartment capable of receiving fluid. The bag compartment has openings defining a first flow port, a second flow port, and an air vent. It has a flexible tube in fluid communication with the first flow port; and a rigid back plate containing securements to couple the blood reservoir, the first flow port, and the flexible tube to the rigid back plate. The rigid back plate contains a clamp situated at the flexible tube, such that a healthcare worker can engage the clamp to completely or partially restrict the fluid flow rate through the flexible tube.

The invention is a soft shell venous reservoir for use in An extracorporeal system that includes a blood reservoir. The blood reservoir comprises at least a first layer of flexible material and a second layer. The first and second layer are sealed together to define a bag compartment capable of receiving fluid. The bag compartment has openings defining a first flow port, a second flow port, an air vent, and a flexible tube in fluid communication with the first flow port. The soft shell venous reservoir may also contain a rigid back plate provided with securements to couple the blood reservoir, the first flow port, the second flow port, an air vent, and the flexible tube to the rigid back plate; and a clamping area attached to the back plate at the securement, coupling the flexible tube to the back plate.

A rigid back plate may be a disposable part of the device or be part of the reusable bracket the device is connected to. A healthcare worker can attach a clamp at the clamping area, and the clamp can be used to control the fluid flow rate through the flexible tube into the first flow port.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A soft shell venous reservoir is typically constructed from a non-porous material that deforms under pressure. The venous bag is often constructed from a material that is at least partially transparent, allowing a healthcare worker to visually monitor the level of blood in the bag. The bag may be constructed for example, from a plastic polymeric material.

Some examples of soft shell reservoir bags can be found in U.S. Pat. No. 5,573,526 by Paul H. Hess entitled SOFT SHELL RESERVOIR and U.S. Pat. No. 5,693,039 by Rodger L. Stewart et al. entitled VENOUS RESERVOIR BAG ASSEMBLY both of which are hereby incorporated by reference. Other examples include the BMR1900™ Soft-Shell Venous Reservoir and CVR 1200 Soft-Shell Venous Reservoir made by Sorin Group Italia S.r.l. both of which are incorporated herein by reference.

Soft shell venous reservoirs often work in combination with a reusable bracket or with a rigid back plate. Because the venous bag is soft and may deform as the amount of blood it holds changes, the reservoir is often coupled to a rigid back plate that provides support for the reservoir and allows it to maintain shape when in use. A back plate may be part of a reusable bracket, allowing the user to connect the soft shell reservoir to the back plate before use. Alternatively, the back plate may be disposable and can also be pre-connected to the soft shell reservoir allowing a user to connect the back plate to the bracket before use. Using a disposable back plate makes the device setup easier for the user.

The back plate or bracket may be attached to a pole located near the heart-lung machine and the venous reservoir attached to the back plate. Alternatively, the back plate may be attached to a pole and the venous bag attached to both the back plate and directly to the pole. Alternatively, the venous bag may be attached directly to the pole with no back plate.

The back plate or bracket can be used to hold the soft reservoir in place, and can also be used to secure the inlet and outlet ports. The back plate will often have cavities or holders molded or attached to it for securing the blood inlet and outlet ports, tubes, vents, and other connections.

The inlet tube can be connected to a Y connector that combines blood flowing from a plurality of feed lines, for example a venous line and a cardiotomy line and channels them both into the venous reservoir through the inlet port. The Y connector is typically a rigid construction that is joined to an inlet port either directly or through an inlet tube.

The rigid Y connector allows tubing such as that used for the venous line and cardiotomy line to be connected by either inserting the tubing into the rigid connector or the rigid connector inserted into the tubing. For example, two Y connectors the EC2100S and EC2191S Y Connector are made by Sorin Group USA, Inc. and incorporated here by reference. In addition to a Y connector, an inlet tube can be constructed to allow for more than two inlet flow lines to be connected and the combined flow directed to the inlet port.

When using a soft shell venous reservoir singly or in combination with a bracket or a rigid back plate, flow control complications may occur. For example, the venous reservoir inlet rigid connector, which includes both the connections to the venous line and the cardiotomy blood lines, is usually structurally integral to the reservoir inlet port. This can make it impossible to partially or totally clamp off the reservoir with only one clamp placed downstream from the Y connection where lines coming from the venous cannulation and the cardiotomy reservoir join together and upstream from the reservoir inlet port. In some instances the inlet port is constructed from material too rigid for easy clamping of the entire port.

In another example, it may also happen that the venous line, connected to the venous cannula, may turn behind the bag, as it must be kept as short as possible. This may result in it ending up located in an area crowded among several tubes making it not easily accessible, for example for clamping. This added complexity may increase the risk of the perfusionist making mistakes.

Moreover, if the venous blood from the patient needs to be temporarily diverted into an additional cardiotomy reservoir, for example to "empty" the patient, there currently is no system for doing that without transiting the blood through the venous reservoir. And doing that requires a complicated clamping maneuver.

Figure 1:
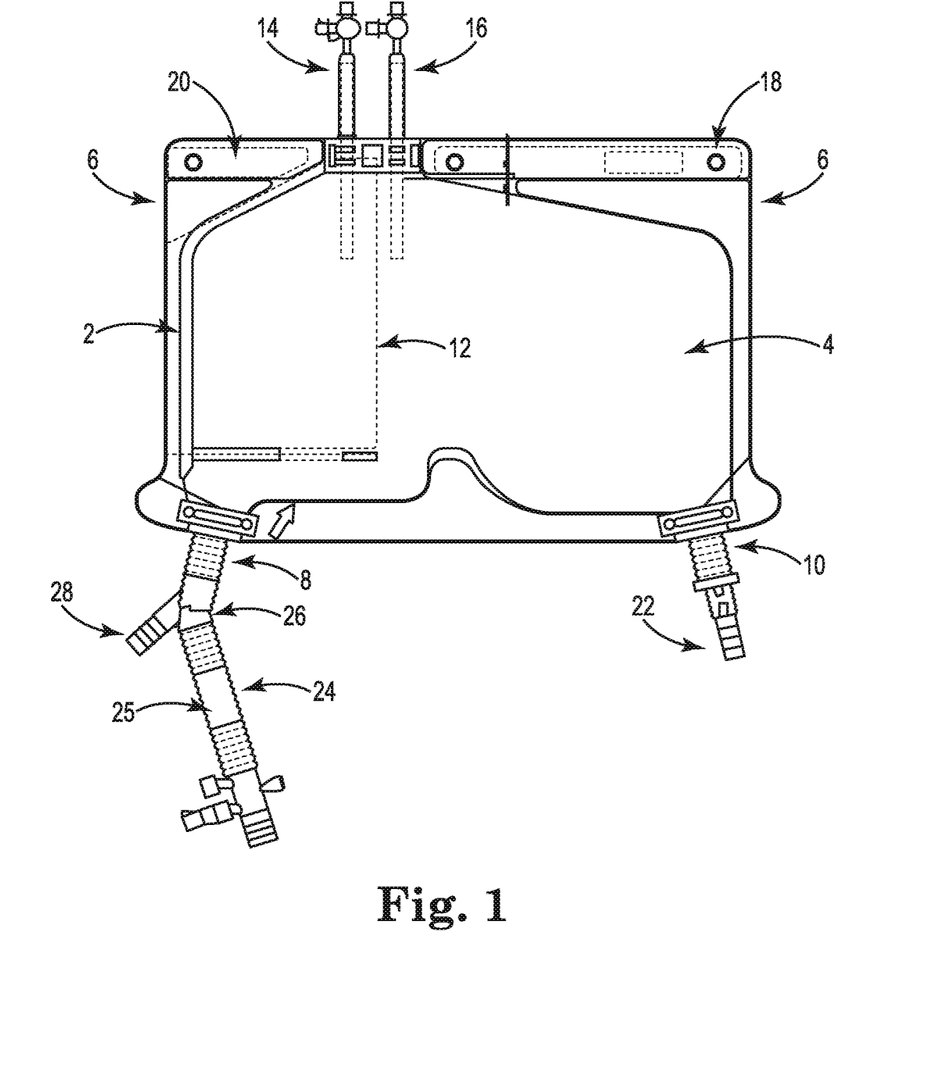
FIG. 1 is a schematic view of the soft shell venous reservoir showing a rigid inlet tube connector.

An example of a soft shell venous reservoir is shown in FIG. 1. The venous reservoir is comprised of a bag 4 shown in FIG. 1 attached to a reusable bracket 6 that acts as a back plate. Blood enters the venous bag 4 through an inlet port 8 and exits through an exit port 10. In some embodiments, a filter 12 is placed between the inlet port 8 and exit port 10 to filter air or embolisms from the blood. Any air removed from the blood will rise to the top of the bag and can exit though any of several ports 14 and 16 that may be provided with stopcocks, allowing a healthcare worker to open or close the purge lines.

The soft shell venous reservoir is typically formed by taking two sheets of a flexible polymer and welding the two sheets together with a heat seal 2 around the periphery. The flexible polymer used is often a vinyl, such as polyvinyl chloride (PVC), but it may be made from other flexible polymers like EVA or polyurethanes. When joining the two sheets together to make the bag 4 often a portion of the two sheets will be additionally welded around the outside of the bag to form a skirt 20. The skirt 20 can be punctured to form eyelets 18. The eyelets 18 can be used to hang the bag either directly onto a stand or to secure the venous reservoir to a back plate. Rigid or semi-rigid materials may be welded or kept between the two polymer foils at the skirt to increase mechanical resistance of the eyelets.

During construction of the bag 4, breaks can be left in the heat seal 2 to allow for openings into the bag 4. At the locations of the openings, the soft shell reservoir material can be welded to ports or tubes creating a leak proof device that can be connected to an extra corporeal circuit. Some of the possible openings that can be created by breaks in the heat seal 2 are an inlet port 8, an outlet port 10, and air vents 14 and 16. In some embodiments there are additional openings to provide alternative options to healthcare workers employing the venous reservoir. In some embodiments, the ports or tubes can be welded. In some embodiments the external perimeter of the bag is welded.

The outlet port 10 is connected to an outlet blood rigid or semi-rigid connector 22, connected to the outlet blood line (not designed) that may carry blood from the outlet port 10 typically to a pump or a pump-head tube or other components of the extracorporeal circulation system.

Blood flows into the venous bag though an inlet port 8. The inlet port 8 may be fed by blood from a single line (not shown), typically a venous line, or from a plurality of blood flow lines. In some embodiments, the soft shell venous reservoir is fed blood from two or more blood lines, for example a venous line 24 and a cardiotomy line 28. Typically a soft shell reservoir is fed by both the venous line 24 and a line coming from an external cardiotomy reservoir where blood sucked from the field by means of the aspirators is collected. Depending on the design of the device, these two lines may be either connected to the arms of a Y connector merging into the reservoir, or merge into the soft shell venous reservoir through two separate inlet tubes.

One embodiment of such a configuration is shown in FIG. 1. In this example, blood is fed from a venous line 24 and a cardiotomy line 28. In this embodiment blood flows from both the venous line 24 and cardiotomy line 28 into a Y connector 26. The Y connector 26 combines the blood flow from the venous line 24 and the cardiotomy line 28 and passes the blood into the inlet port 8. The combined blood can then flow through the inlet port 8 into the venous bag 4.

In FIG. 1, only the venous line 24 has a clamp area 25. In such a device, the venous and cardiotomy lines can only be simultaneously clamped by using two different clamps. The clamp on the venous line 24 is used to regulate the blood flow from the patient. The clamp in the cardiotomy line 28 is used to close or open the cardiotomy line. It is not possible with this design to provide direct communication between the venous and cardiotomy line, while restricting flow to the soft shell venous reservoir, thus the need for the current invention.

The clamp area 25 may be a tube constructed with flexible material that can be constricted by a clamp from the outside of the tube. The clamp may be attached to the venous line 24 to prevent or regulate blood flow through the venous line 24 to the inlet port 8. A flow restrictor may be a separate component to the cardiotomy line 28 to prevent or regulate blood flow through the cardiotomy line.

Figure 2:
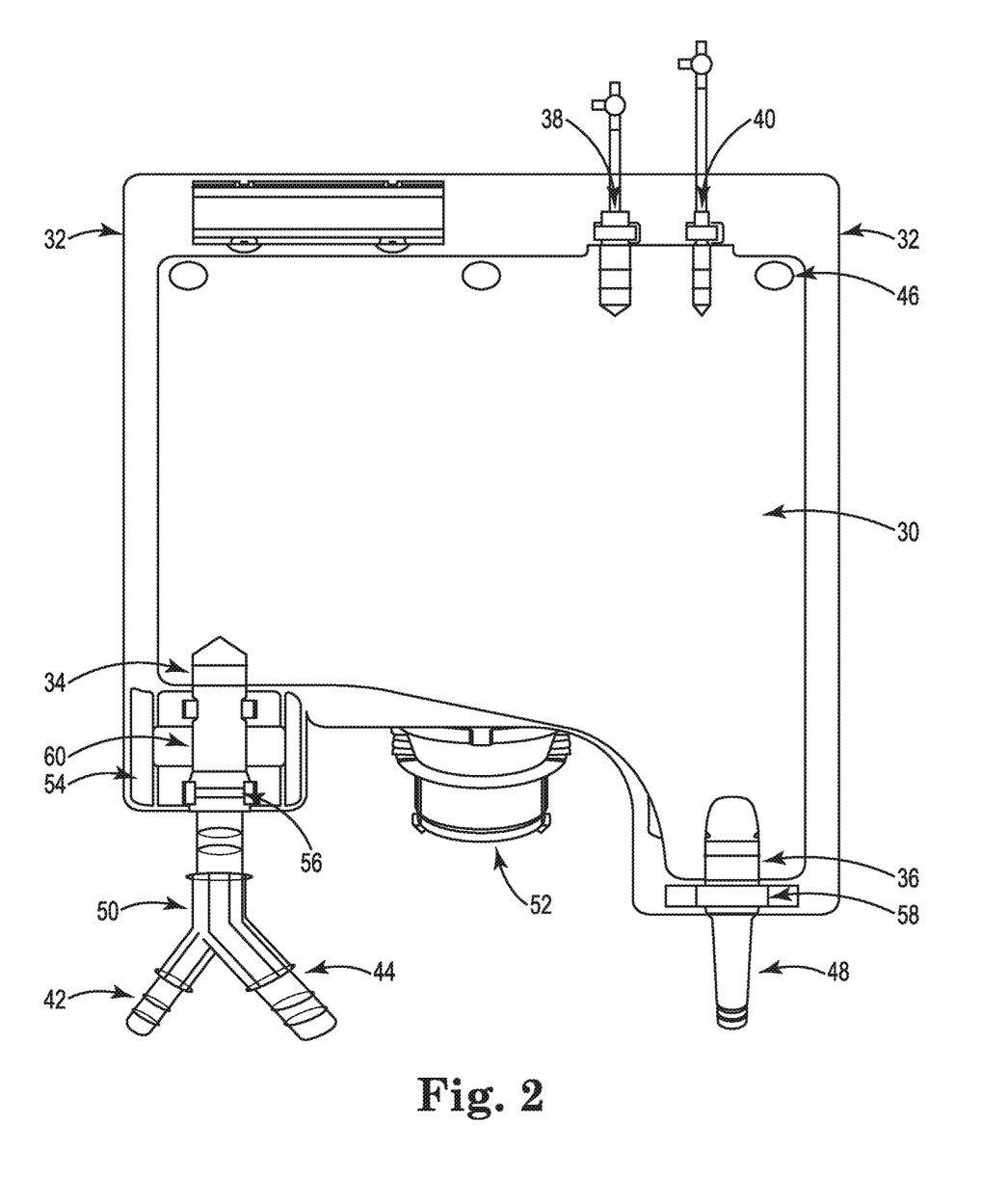
FIG. 2 is a schematic view of a soft shelled venous reservoir with a clamping area and related cavity in accordance with the current invention.

FIG. 2 shows a venous reservoir 30 attached to a back plate 32 with the back plate including a component 52 for integrating the device to an oxygenator or connecting the device to a reusable bracket. The venous reservoir 30 may be attached to the back place 32 using eyelets 46 constructed into the venous reservoir 30. The back plate 32 aids in maintaining the shape of the venous reservoir 30.

Air vents 38 and 40 allow air to be released from the top of the bag 30. The air vents 38 and 40 may be manually opened or can be set to vent when air reaches a certain level or pressure.

An exit port 36 is shown attached to an exit connector 48. The exit port 36 allows blood to exit the venous reservoir 30 and return either to the pump or head-pump tube or to other components of the extracorporeal blood circuit.

An inlet port 34 is shown attached to an inlet line 56. An inlet line 56 may be constructed to be fed by one blood flow line or may be fed by a plurality of blood flow lines. One embodiment shown in FIG. 2 is fed by two blood flow lines. The two blood flow lines are combined using a Y connector 50 that receives blood flow from two blood flow lines and feeds the combined flow into the inlet line 56. In other embodiments, an alternative connector can be used to combine blood flow from two, three, or more blood flow lines and feeding the combined blood flow into the inlet line 56.

While one inlet port 34 and one exit port 36 are shown, certain embodiments may contain more than one inlet port and/or more than one outlet port. Alternatively, while two air vents 38 and 40 are shown in FIG. 2 a venous reservoir with one or more air vents may be incorporated.

In one embodiment, a back plate 32 includes an empty area 54 in the back plate 32 that allows for the possibility to position a clamp at a clamping area 60, surrounding the inlet line 56 that partially or completely restricts blood flow to the inlet port 34. The clamp may be positioned downstream from the Y connector 50. In this configuration, blood flow from all blood flow lines to the inlet port 34 is restricted.

In another embodiment of the invention an inlet line 56 is constructed from relatively soft material, such as polyvinyl chloride (PVC), that allows the inlet line 56 to be clamped using an clamp that encloses the inlet line 56 and compresses the inlet line 56 from the outside.

In another embodiment, an inlet line 56 may be constructed with a stopcock type clamp that allows a healthcare worker to regulate flow through the inlet line 56 by turning the stopcock.

In another embodiment, a back plate 32 may be constructed with a clamp 60 attached to the back plate 32 and surrounding the inlet line 56. The clamp 60 may be constructed to allow a healthcare worker to activate the clamp 60 by compressing the clamp 60 against the back plate 32 and restricting blood flow from the Y connector 50 to the inlet port 34.

In another embodiment, a back plate 32 may contain an empty area 54 that may positon the inlet line 56 within the clamping area 60. The clamping area 60 may be constructed with a disposable clamp attached. In such an embodiment a healthcare worker may position the venous reservoir 30 to the back plate 32 and the inlet line 56 may be secured within the clamping area 60. With such a configuration, a healthcare worker can use the clamp that is provided with the back plate 32. For example, a clamp may be constructed to compress the inlet line 56 against the back plate 32.

FIG. 2 illustrates an embodiment where the back plate 32 may be constructed with a clamping area 60 that has a clamp not attached to the back plate. Potentially, with an automatic mechanism, three clamps could be positioned: one clamp on the venous line 44, to regulate the flow of the venous blood coming from the patient, one clamp in correspondence with the cardiotomy line 42, to close or open communication between cardiotomy line 42 and the soft-shell venous reservoir, and one clamp in the clamping area 60, that could regulate the combined flow coming from the venous and cardiotomy lines. If the cardiotomy line 42 is not closed, this configuration could put the venous line 44 and the cardiotomy line 42 in direct communication, excluding the soft venous reservoir. This configuration is not currently possible with devices present on the market today.

In one embodiment a back plate 32 may be constructed with cavities or recesses to receive one or all of the air vents 38 and 40, inlet port 34, and 36 or any combination.

In another embodiment the back plate may be integrally molded in a single piece to provide securements for one or all of the air vents 38 and 40, inlet port 34, and 36 or any combination.

In another embodiment the back plate may be constructed to allow the back plate 32 to be combined with attachments for securing one or all of the air vents 38 and 40, inlet port 34, and exit port 36 or any combination.

Restricting blood flow from the Y connector 50 to the inlet port 34 using only one clamp allows a healthcare worker to control blood flow into the venous reservoir 30 with one intuitive movement. Using one clamp also allows a healthcare worker to completely restrict blood flow into the venous reservoir 30 without having to clamp more than one line, thus reducing the time required to shut off blood flow into the venous reservoir. Also, having the clamp positioned downstream from the Y connector 50 allows a healthcare worker the option of diverting blood flow from either the venous line 42 directly into the cardiotomy line 44 or from the cardiotomy line 44 to the venous line 42 through the Y connector.

Figure 3:
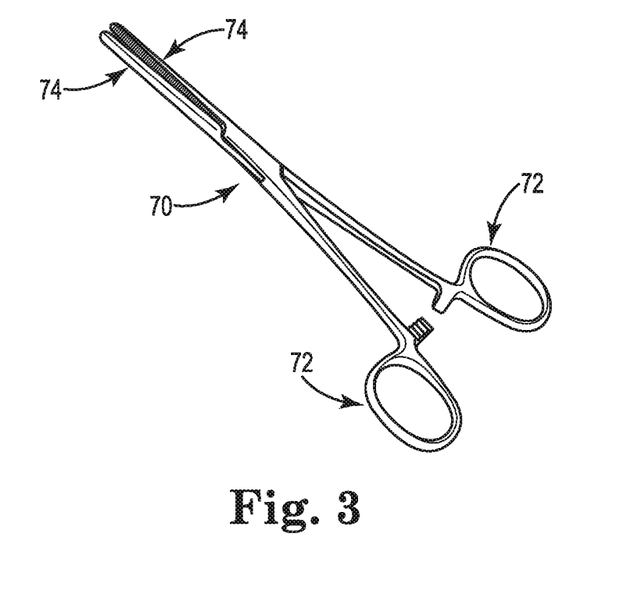
FIG. 3 is a schematic view of a manual clamp.

FIG. 3 shows a clamp 70 that may be used to close any of the inlet line 56, the cardiotomy line 42, or the venous line 44. A clamp can be manipulated to shut off flow through a flow line. A sample embodiment shows a clamp 60 with a handle 72 that can be manipulated by a healthcare worker. The handle 72 operates arms 74 that can compress together to clamp a tube such as the inlet line 56 closed.

Figure 4:
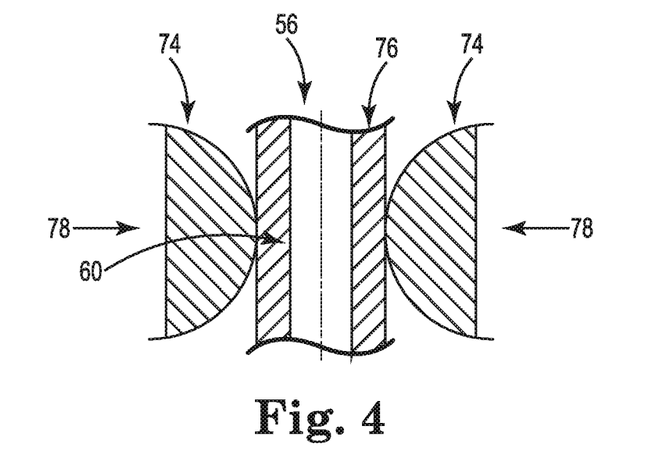
FIG. 4 is a schematic view of an inlet line with clamp arms positioned on two sides of the inlet line.
Figure 5A:
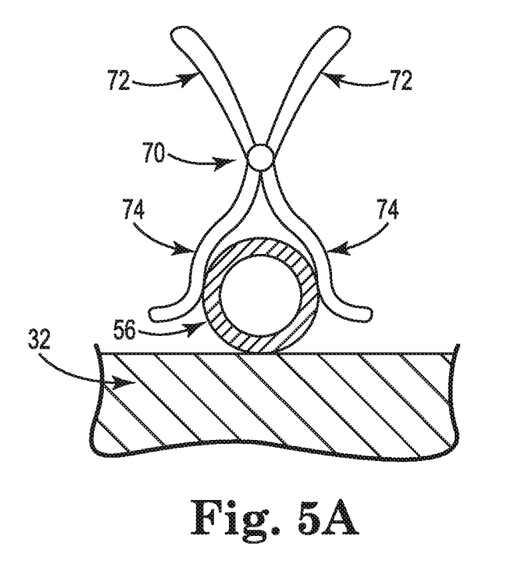
FIG. 5A is a schematic shown from the inlet line axial direction with an open clamp around the inlet line.
Figure 5B:
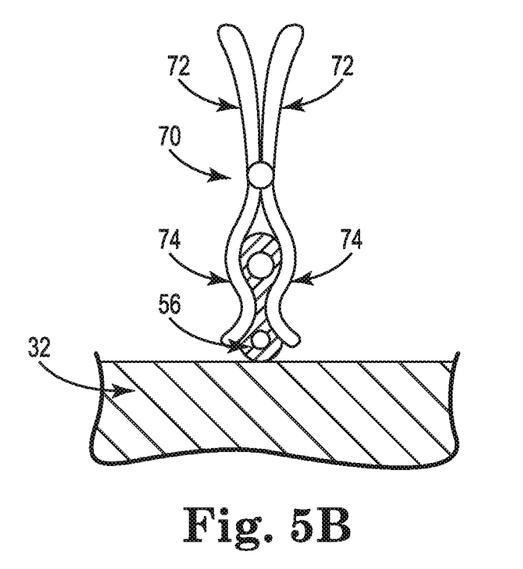
FIG. 5B is a schematic shown from the inlet line axial direction with a closed clamp clamping the inlet line.

FIGS. 4, 5A, and 5B illustrate how a clamp may be used to shut off flow through a tube such as the inlet line 56.

FIG. 4 illustrates an inlet line 56 that has a wall 76 constructed with flexible material at a clamping area 60. A clamp may be positioned so the arms 74 are positioned on both sides of the inlet line 56 at the clamping area 60. When a force 78 is directed inward toward the tube at the clamping area 60 the force causes the tube to collapse. In this case the inlet line 56 is compressed.

FIG. 5A is a view of the inlet line 56 looking in the axial direction of the inlet line 56. FIG. 5A illustrates an open clamp 70 positioned around the inlet line 56. The clamp 70 is manipulated by a healthcare worker by working the handles 72 to position the arms 74 around the inlet line 56 as the inlet line 56 is positioned against the back plate 32. In some embodiments the clamp may be connected to a back plate as part of a disposable assembly, allowing it to be set up in the correct position for use by a heath care worker.

FIG. 5B is a view of the inlet line 56 looking in the axial direction of the inlet line 56 with the clamp 70 closed. A healthcare worker can manipulate the clamp handle 72 to close the clamp arms 74 which compress the inlet line 56 and closes it off which restricts blood flow through the inlet line 56. In some embodiments a disposable assembly may be constructed with a clamp attached to a back plate, providing a healthcare worker with the clamp in the correct position.

In an alternative embodiment (not shown), where the connector combines blood flow from two, three, or more blood flow lines, a clamp may be positioned at the connector anywhere between the two, three, or more blood flows. This embodiment allows a healthcare worker to selectively restrict blood flow from any combination of the blood flow lines.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A soft shell venous reservoir for use in an extracorporeal circulation system of the type including:
   a blood reservoir;
   the blood reservoir comprising at least a first layer of flexible material and a second layer, the first and second layers sealed together to define a bag compartment capable of receiving fluid, the bag compartment having openings defining a single inlet port, an exit port, and an air vent;
   a flexible tube coupled to the single inlet port and in fluid communication with the single inlet port;
   a clamp situated at the flexible tube, such that a healthcare worker can engage the clamp to control the fluid flow rate through the flexible tube and the single inlet port;
   a rigid back plate containing securements to couple the blood reservoir, the single inlet port, and the flexible tube to the rigid back plate, the rigid back plate comprising an empty area configured for positioning the clamp at the flexible tube; and
   a fluid line connector configured to combine multiple inlet fluid lines in fluid communication with the single inlet port, the flexible tube being located in between the fluid line connector and the single inlet port,
   wherein the clamp is configured to be movable to positions upstream and downstream from the fluid line connector, such that the healthcare worker can engage the clamp to restrict blood flow into the reservoir.

2. The soft shell venous reservoir as in claim 1, wherein the fluid line connector comprises a Y connector.

3. The soft shell venous reservoir as in claim 1, wherein the clamp is configured to completely surround the flexible tube.

4. The soft shell venous reservoir as in claim 1, wherein the clamp does not completely surround the flexible tube when not restricting flow through the flexible tube.

5. The soft shell venous reservoir as in claim 1, wherein the second layer of the bag compartment includes a rigid material.

6. The soft shell venous reservoir as in claim 1, wherein the bag compartment includes a rigid material.

7. A clampable soft shell venous reservoir comprising:
   a blood reservoir;
   the blood reservoir comprising a first and second layer of flexible material sealed together to define a bag compartment capable of receiving fluid, the bag compartment having openings defining a single inlet port, an exit port, and an air vent;
   a flexible tube coupled to the single inlet port and in fluid communication with the single inlet port;
   a rigid back plate containing securements to couple the blood reservoir, the single inlet port, and the flexible tube to the rigid back plate;
   a clamp movably attached to the rigid back plate and situated at the flexible tube, such that a healthcare worker can engage the clamp to completely or partially restrict the fluid flow rate through the flexible tube and the single inlet port; and
   a rigid fluid line connector configured to combine multiple inlet fluid lines in fluid communication with the single inlet port, the flexible tube being located in between the rigid fluid line connector and the single inlet port,
   wherein the clamp is located downstream from the rigid fluid line connector, such that the healthcare worker can engage the clamp to restrict blood flow into the blood reservoir.

8. The clampable soft shell venous reservoir as in claim 7, wherein the clamp is configured to completely surround the flexible tube.

9. The clampable soft shell venous reservoir as in claim 7, wherein the clamp does not completely surround the flexible tube when not clamping the flexible tube.

10. A soft shell venous reservoir for use in an extracorporeal circulation system of the type including:
   a blood reservoir;
   the blood reservoir comprising at least a first layer of flexible material and a second layer, the first and second layer sealed together to define a bag compartment capable of receiving fluid, the bag compartment having openings defining a single inlet port, an exit port, and an air vent;
   a flexible tube coupled to the single inlet port and in fluid communication with the single inlet port;
   a rigid back plate containing securements to couple the blood reservoir, the single inlet port, the exit port, the air vent, and the flexible tube to the rigid back plate;
   a clamping area attached to the back plate to secure the flexible tube to the back plate, the clamping area configured to accommodate a clamp such that a healthcare worker can attach the clamp at the clamping area to the flexible tube to control the fluid flow rate through the flexible tube into the single inlet port; and
   a multiple tube connector configured such that a plurality of flow lines can be joined in fluid communication with the flexible tube, the flexible tube being located in between the multiple tube connector and the single inlet port,
   wherein the clamp is located downstream from the multiple tube connector, such that the healthcare worker can engage the clamp to restrict blood flow into the blood reservoir.

11. The soft shell venous reservoir as in claim 10, wherein the clamping area is configured to accommodate the clamp completely surrounding the flexible tube.

12. The soft shell venous reservoir as in claim 10, wherein the clamping area is configured to accommodate the clamp not completely surrounding the flexible tube.

* * * * *